(12) United States Patent
Chen

(10) Patent No.: US 6,455,464 B1
(45) Date of Patent: Sep. 24, 2002

(54) PREPARATION AND USE OF NON-CHROME CATALYSTS FOR CU/CR CATALYST APPLICATIONS

(75) Inventor: Jianping Chen, Erie, PA (US)

(73) Assignee: Engelhard Corporation, Iselin, NJ (US)

( * ) Notice: Subject to any disclaimer, the term of this patent is extended or adjusted under 35 U.S.C. 154(b) by 0 days.

(21) Appl. No.: 09/142,987
(22) PCT Filed: Mar. 21, 1997
(86) PCT No.: PCT/US97/04678
§ 371 (c)(1),
(2), (4) Date: Sep. 18, 1998
(87) PCT Pub. No.: WO97/34694
PCT Pub. Date: Sep. 25, 1997

Related U.S. Application Data
(60) Provisional application No. 60/013,824, filed on Mar. 21, 1996.

(51) Int. Cl.$^7$ ................................................. B01J 23/72
(52) U.S. Cl. ........................ 502/346; 502/344; 502/348
(58) Field of Search ................................ 502/344, 346, 502/355

(56) References Cited

U.S. PATENT DOCUMENTS

| | | |
|---|---|---|
| 2,091,800 A | 8/1937 | Adkins et al. |
| 3,787,332 A * | 1/1974 | Sugier .................. 502/346 |
| 3,865,753 A | 2/1975 | Broecker et al. |
| 3,899,446 A | 8/1975 | Miya et al. |
| 3,935,128 A | 1/1976 | Fein |
| 3,988,263 A * | 10/1976 | Hansford .................. 502/346 |
| 4,252,689 A | 2/1981 | Miya |
| 4,278,567 A | 7/1981 | Miya et al. |
| 4,302,597 A | 11/1981 | Manara et al. |
| 4,308,176 A | 12/1981 | Kristiansen |
| 4,450,245 A | 5/1984 | Adair et al. |
| 4,551,444 A | 11/1985 | Lin et al. |
| 4,631,266 A * | 12/1986 | Wold et al. .................. 502/324 |
| 4,977,123 A * | 12/1990 | Flytzani-Stephanopoulos et al. ..... 502/84 |
| 4,982,020 A | 1/1991 | Carduck et al. |
| 5,053,380 A | 10/1991 | Wegman et al. |
| 5,243,095 A | 9/1993 | Roberts et al. |
| 5,298,472 A | 3/1994 | Wegman et al. |
| 5,418,201 A | 5/1995 | Roberts et al. |
| 5,587,135 A | 12/1996 | Fetzer et al. |

FOREIGN PATENT DOCUMENTS

| | | |
|---|---|---|
| EP | 0042471 | * 12/1981 |
| EP | 0691157 | 6/1995 |
| EP | 0695579 | 7/1996 |
| SU | 0829621 | 5/1981 |

OTHER PUBLICATIONS

Glankler, C.W., J. Am Oil Chemist' Soc., vol. 56, (Nov. 1979) pp. 802A–805A.

* cited by examiner

Primary Examiner—Elizabeth D. Wood
(74) Attorney, Agent, or Firm—Polster, Lieder, Woodruff & Lucchesi

(57) ABSTRACT

A non-chrome, copper-containing catalyst, Cu—Al—O and method of preparing the same are provided wherein the Cu—Al—O catalyst is prepared by the co-precipitation of copper nitrate ($Cu(NO_3)_2$) and sodium aluminate ($Na_2Al_2O_4$) solutions using sodium carbonate ($Na_2CO_3$) as a precipitant. the precipitate is filtered, washed to remove excess sodium, and dried. The dried product, to be used in a powder form, is calcined at a preferred temperature of approximately 700 to 900° C. for approximately 1 to 4 hours. The dry powder, to be tableted or extruded, is calcined at a temperature of approximately 400 to 700° C. The activity of the Cu—Al—O catalyst can be promoted in hydrogenolysis applications by the addition of various agents. The Cu—Al—O catalyst can be employed in applications in place of Cu/Cr, or other copper-based catalysts.

38 Claims, 6 Drawing Sheets

A=ID# 008
B=ID# 007
C=ID# 006
D=ID# 005
E=ID# 004
F=ID# 003
G=ID# 002

PREPARATION AND USE OF NON-CHROME CATALYSTS FOR CU/CR CATALYST APPLICATIONS

This application claims benefit of Provisional Application 60/013,824 filed Mar. 21, 1996.

BACKGROUND OF THE INVENTION

This invention relates generally to catalyst compounds and, more specifically to the preparation and characterization of Cu—Al—O catalysts to replace Cu/Cr catalysts in specific applications.

The commercial catalysts for hydrogenolysis of carbonyl groups in organic compounds have been dominated by Adkins' catalyst since the 1930's (H. Adkins, R. Connor, and K. Folkers, U.S. Pat. No. 2,091,800 (1931)). The Adkins' catalyst is a complex mixture of primarily copper oxide and copper chromite. The catalyst is used in hydrogenolysis reactions, for example the catalytic hydrogenolysis of an ester to alcohols, illustrated generally by the following reaction:

Under reaction conditions it is believed that the catalyst reduces to a mixture of metal copper, cuprous oxide and copper chromite. One of the crucial roles of chrome in Cu/Cr catalysts is that it behaves as a structural promoter.

The Cu/Cr catalysts have widespread commercial and industrial application in such diverse processes as hydrogenation of aldehyde in oxoalcohol finishing, hydration of acrylonitrile, fatty acid hydrogenolysis, hydrogenolysis of methyl esters, reductive amination, and a myriad of other hydrogenation and oxidation reactions such as are listed below. U.S. Pat. No. 3,935,128, to Fein et al, provides a process for producing a copper chromite catalyst. U.S. Pat. No. 4,982,020 to Carduck et al., discloses a process for direct hydrogenation of glyceride oils where the reaction is carried out over a catalyst containing copper, chromium, barium and/or other transition metals in the form of oxides which, after calcination, form the catalyst mass. U.S. Pat. No. 4,450,245 to Adair et al., provides a catalyst support wherein the catalyst is employed in the low temperature oxidation of carbon monoxide, another important application of such catalysts.

Environmental issues involving disposal of chrome-containing catalysts, however, are expected to eventually eliminate their use in many countries. Additionally, catalyst activity is one of the most important factors determining a catalyst's performance. It is, therefore, advantageous to employ non-chrome, copper-containing catalysts having good catalyst activity to replace currently used Cu/Cr catalysts in hydrogenation, alkylation and other reactions.

Several prior art, non-chrome containing catalysts are known. For example, U.S. Pat. No. 5,418,201, to Roberts et al., discloses hydrogenation catalysts in powdered form and method of preparing a hydrogenation catalysts comprising oxides of copper, iron, aluminum and magnesium. U.S. Pat. No. 5,243,095 also to Roberts et al. provides for the use of such copper, iron, aluminum and magnesium catalysts in hydrogenation conditions.

U.S. Pat. No. 4,252,689 to Bunji Miya, describes a method of preparing a copper-iron-alumina catalyst used in hydrogenation. U.S. Pat. No. 4,278,567 to Bunji Miya et al., discloses a similar process for making a copper-iron-aluminum catalyst. U.S. Pat. No. 4,551,444 to Fan-Nan Lin et al., provides a five-component catalyst wherein the essential components are copper, an iron group component, a component of elements 23–26, an alkali metal compound and a precious metal compound.

C. W. Glankler, Nitrogen Derivatives (Secondary and Tertiary Amines, Quarternary Salts, Diamines, Imidazolines), *J Am. Oil Chemists' Soc.*, November 1979 (Vol 56), pages 802A–805A, shows that a copper-chromium catalyst is used to retain coarbon to carbon unsaturation in the preparation of nitrogen derivatives. U.S. Pat. No. 4,977,123 to Maria Flytzani Stephanopoulos et al., discloses extruded sorbent compositions having mixed oxide components of copper oxide, iron oxide, and alumina. U.S. Pat. No. 3,865,753, to Broecker et al, provides a process for preparing a nickel magnesium aluminum catalyst used for the cracking of hydrocarbons. The prior art, non-chrome containing catalysts have several disadvantages that limit the industrial applicability of the catalysts.

An ideal catalyst should be both chemically and physically stable. Chemical stability is demonstrated by consistent catalyst activity in an acceptable time period. Physical stability is demonstrated by maintaining a stable particle size or physical form during the chemical reaction. Moreover, an ideal catalyst would have narrow particle distribution since particle size affects filtration speed in a commercial process employing the catalysts. The stability is further demonstrated by resistance to common poisons such as sulfur compounds, organic chlorines, bromine and iodine compounds. Generally, stability is tested using Cu/Cr catalyst as the standard catalyst.

An ideal catalyst also would have a low percentage of leachable cations. This ensures the maintenance of catalyst activity and a good product quality.

Furthermore, it is important the catalyst function well in commercial applications. For example, the hydration of acrylonitrile to acrylamide over a copper-containing catalyst is an important industrial application. Several different copper catalysts have been developed for this application, as indicated by the prior art patents. The catalysts include copper/chrome, copper/silica, copper on kieselguhr, Raney copper, ion exchange copper on silica and copper on alumina catalysts. Most of the prior art catalysts used in this application have the problem of deactivation. The catalyst is deactivated by the accumulation of polyacrylamide on the surface or by the oxidation of surface copper. Selectivity is also important. Normally, hydration of C—N bonds is favored by acidic oxides while hydrolysis of C—C bonds is favored by basic oxides. Therefore, the surface acidity of the catalyst is crucial to this application.

For some other applications that require some surface basicity, alkaline metal or alkaline metal compounds should be remained or added to the catalyst matrix.

SUMMARY OF THE INVENTION

It is among the principal objects of the present invention to provide a non-chrome, copper-containing catalyst that can be employed as a catalyst in place of Cu/Cr catalysts in new or conventional chemical reactions.

It is another object of the present invention to provide a non-chrome, copper-containing catalyst that exhibits comparable or superior activity and selectivity to conventional Cu/Cr catalysts in a numerous chemical reactions.

Another object of the present invention is to provide a non-chrome, copper-containing catalyst having a spinel crystal structure analogous to the spinel crystal structure of conventional Cu/Cr catalysts.

Still another object of the invention to provide a non-chrome, copper-containing catalyst that contains an optimal ratio of copper to alumina. Yet another object of the present invention is to provide a non-chrome, copper-containing catalyst thereby eliminating the environmental issues associated with the disposal of chrome-containing catalysts.

A still further object of the invention is to provide a non-chrome, copper-containing catalyst that is relatively stable, and has a low percentage of leachable cations.

Still another object of the present invention is to provide a non-chrome, copper-containing catalyst that is efficient to prepare, functions well as a Cu/Cr catalyst in new or conventional chemical reactions, has good selectivity and is not easily deactivated.

In accordance with one aspect of the invention, a non-chrome, copper-based catalyst, Cu—Al—O, and a method of preparing the same are provided wherein the catalyst is prepared by co-precipitation from a solution consisting essentially of a soluble copper salt and a soluble aluminum compound in the presence of a precipitating agent. The copper salt is illustratively cupric nitrate, $Cu(NO_3)_2$, and the aluminum compound is preferably a basic aluminum salt, most preferably an aluminate such as sodium aluminate, $Na_2Al_2O_4$. The copper salt and the aluminum compound are preferably dissolved separately and the solutions are slowly mixed in an aqueous precipitation mixture in approximately 5 minutes to 12 hours, more preferably in approximately 0.5 to 2 hours. The precipitant is preferably added to the precipitation mixture to maintain a pH of about 6.5 to 8.5, most preferably 7.4±0.5. The precipitant is illustratively sodium carbonate, $Na_2CO_3$. The precipitate is filtered, washed to removed excess sodium, and dried, preferably at a temperature of from room temperature to about 150° C., most preferably between about 100° C. and 150° C. The dried product is then calcined at a temperature ranging from about 300° C. to about 1000° C., the temperature of calcining being chosen to give the catalyst desired properties. The dried product, to be used in a powder form, is calcined at a preferred temperature of approximately 700° C. to 900° C. for approximately 0.5 to 4 hours. The dry powder, to be extrudated, after drying is then mixed with water to a desired water content. The dry powder, to be tableted, is calcined at a temperature of approximately 400° C. to 700° C.

The preferred catalysts of the present invention are generally homogeneous compositions having an aluminum content expressed as $Al_2O_3$ greater than about 20% by weight, preferably about 25% to about 70% by weight, and more preferably about 30% to about 60%. The copper content expressed as CuO is less than about 80% by weight, preferably about 40% to about 70% by weight. This convention is used throughout this patent, unless noted otherwise. The catalysts are generally homogeneous, rather than being supported by a heterologous matrix. The catalysts show a spinel structure when calcined above about 700° C. Although the catalysts calcined at lower temperatures show no x-ray diffraction patterns characteristic of a spinel, and although they have different characteristics, such as higher leachable cations, they nonetheless show remarkable catalytic activity and selectivity in numerous reactions.

The Cu—Al—O catalyst produced by the method of the invention has been found to be comparable with or favorable to commercial Cu/Cr catalysts widely used in numerous hydrogenation and hydrogenolysis reactions, in terms of the most important characteristics of a commercial catalyst. In many reactions it has been found to have a far greater activity than commercially available Cu/Cr catalysts, and a remarkable selectivity. In extruded or tableted form, they have high side crush strength. They have high pore volumes, typically exceeding 0.25 ml/g. The powder form catalyst has high filtration rates. They resist poisoning. They have low cation extractability.

The solid catalyst formed as an extrudate of the catalyst of the present invention is preferably formed from a Cu—Al—O powder with LOD of thirty to fifty percent, the extrudate being formed with and without binder or lubricant. The extrudate has a pore volume of approximately 0.15 ml/mg to approximately 0.7 ml/g, preferably greater than 0.3 ml/g. The extrudate has a bulk density of approximately 0.6 g/ml to approximately 1.0 g/ml and a surface area of from 15 $m^2$/g to 250 $m^2$/g. The preferred extrudate has a bimodal pore size distribution centering around 100 Å and around 1000 Å to 2000 Å.

When formed as a tablet, the catalyst has a pore volume greater than about 0.25 ml/g and a bulk density of approximately 0.8 g/ml to approximately 1.5 g/ml. The activity of the Cu—Al—O catalysts of the present invention can be increased in hydrogenolysis and other applications by the addition of promoters such as Ce, Mn, Ba, Zn, Co, and Ni compounds in amounts less than 50% by weight, preferably less than 25% by weight. In some applications the promoter is preferably less than 5% by weight, and most preferably between 0.1% and 2.5% by weight. The presence of alkaline metal compounds will improve selectivity in some applications.

DETAILED DESCRIPTION OF THE INVENTION

Figure 1:
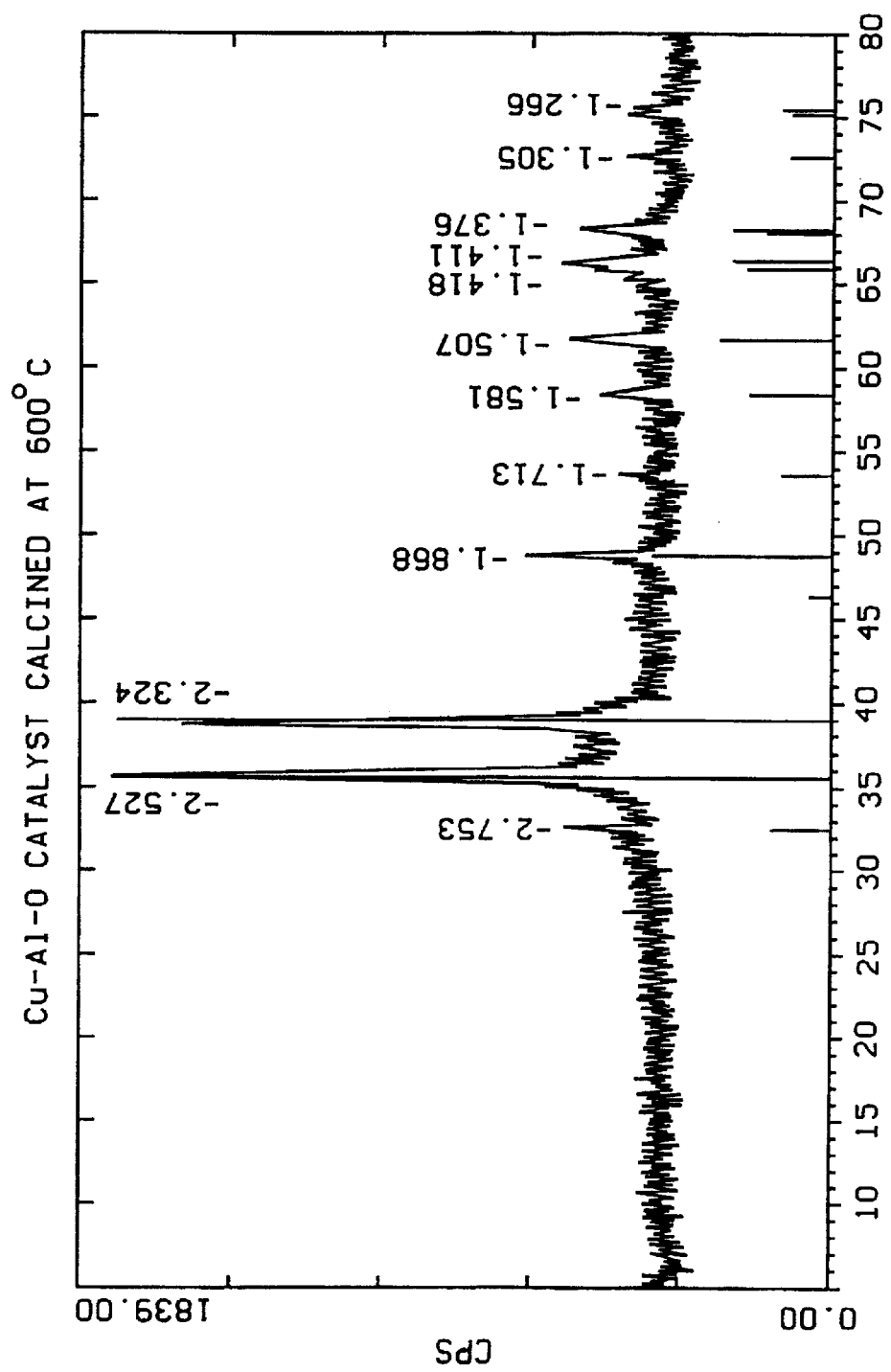
FIG. 1 illustrates the x-ray diffraction of the Cu—Al—O catalyst calcined at 600° C.

The present invention contemplates a catalyst, Cu—Al—O, the method of preparing the Cu—Al—O catalyst by the co-precipitation of copper nitrate and sodium aluminate using soda ash (sodium carbonate) as a precipitant, and applications employing the Cu—Al—O catalyst. The preparation of the catalyst is best illustrated by the following examples:

PREPARATION OF CU—AL—O CATALYST

EXAMPLE 1

The Cu—Al—O catalyst of the present invention was prepared as follows:

Weigh out 1640 g of copper nitrate solution (15.48% Cu) and dilute with deionized water to 2500 ml. Weigh out 815.6 g sodium aluminate (25% $Al_2O_3$) and dilute with deionized water to 2500 ml. Add 2500 ml deionized water to a 12 liter tank. Weigh out 318 g sodium carbonate (soda ash) and dissolve in deionized water to 1500 ml. Simultaneously add the copper nitrate solution and sodium aluminate solution to the 2500 ml of deionized water. The copper nitrate and sodium lo aluminate solutions may be added at a rate of 33 ml per minute. Add the sodium carbonate (soda ash) solution to the mixture, keeping the slurry at a constant pH ranging from approximately 6.0 to 8.5, preferably about 7.4, by adjusting the rate of addition of the soda ash solution. The precipitation can be carried out at a wide range of temperatures from room temperature to 90° C. or more. Typically the precipitation is carried out at room temperature. Filter the slurry to form a filter cake. Wash the filter cake with 3000 ml of deionized water three or more (preferably four) times. Dry the filter cake at 120° C. overnight. Calcine the dried Cu—Al—O powder at 400° C. for two hours. Do the following testing and characterization on this calcined powder: particle size distribution, acetic acid soluble cations, surface area, x-ray diffraction (XRD), thermal gravimetric analysis (TGA) and hydrogenolysis of coconut fatty acid activity test.

EXAMPLES 2–7

The following examples 2–8 were carried out in the same manner as example 1, except that the dried Cu—Al—O powder was calcined for two hours in air at the temperatures given below:

Example 2 500° C.

Example 3 600° C.

Example 4 700° C.

Example 5 800° C.

Example 6 900° C.

Example 7 1000° C.

CHARACTERIZATION OF Cu—Al—O CATALYST PREPARED BY EXAMPLES 1–7

EXAMPLE 8

Leachable Catalyst Cations

The leachable cations measurements are performed by reacting 100 ml 10% acetic acid with 10 g of powder catalyst for one hour with continuous stirring. The solution is separated, filtered and washed. The cation content in the solution is quantitatively analyzed.

The following Table 1 illustrates the leachable copper (Cu) and aluminum (Al) in catalyst prepared at different calcination temperatures. A commercially available Cu/Cr catalyst was also tested for comparison.

As illustrated in the above table, if the catalyst is calcined at 400° C.(Example 1), the leachable Cu is 27%. The leachable Cu dropped to <5% if the catalyst is calcined at a temperature higher than 700° C. (Example 5–7). Therefore, the leachable Cu content can be controlled by calcination temperature.

EXAMPLE 9

Characterization of the Cu—Al—O Catalysts by X-Ray Diffraction (XRD)

Figure 2:
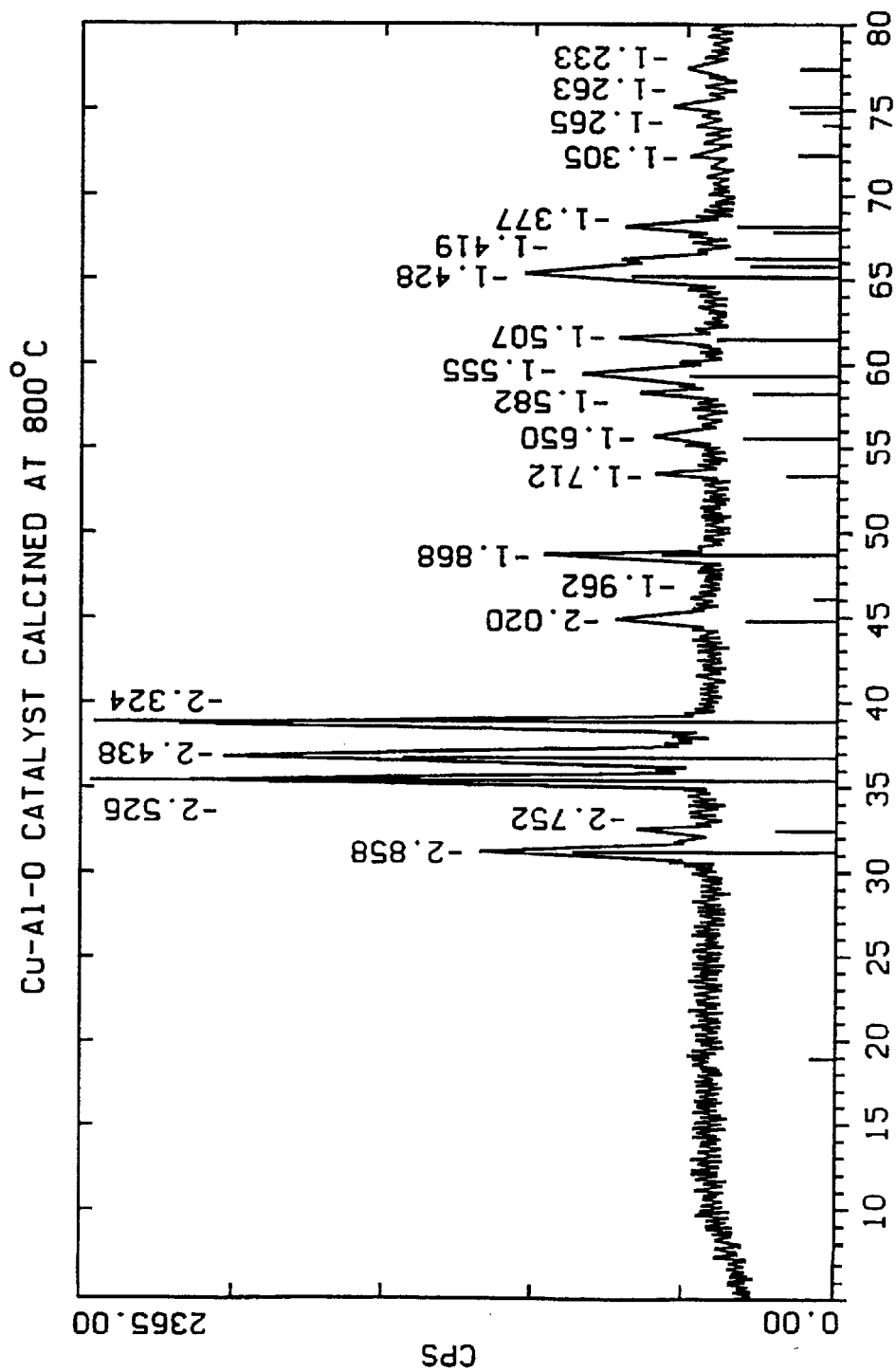
FIG. 2 illustrates the x-ray diffraction of the Cu—Al—O catalyst calcined at 800° C.

FIGS. 1 and 2 are XRD analyses of the Cu—Al—O catalysts of the present invention calcined at different temperatures. XRD analysis results illustrate that the catalysts are nearly amorphous when calcined at temperatures below 500° C. (Examples 1–2). FIG. 1 shows that At 600° C. (Example 3), the diffraction pattern corresponding to CuO phase appears. At this temperature, CuO is the only crystalline phase detected.

As shown in FIG. 2, when calcination temperatures are increased to 700° or 800° C. (Examples 4–5), in addition to CuO formation, a new spinel crystalline phase corresponding to copper aluminate ($CuAl_2O_4$) appears. By comparing the XRD data with the results of Table 1 and Table 17, it can be seen that the formation of crystalline CuO and $CuAl_2O_4$ in the Cu—Al—O catalyst not only decreases the catalyst leachable cations, but also increases catalyst activity.

EXAMPLE 10

Characterization of the Cu—Al—O Catalyst by Thermal Gravimetric Analysis (TGA)

Figure 3:
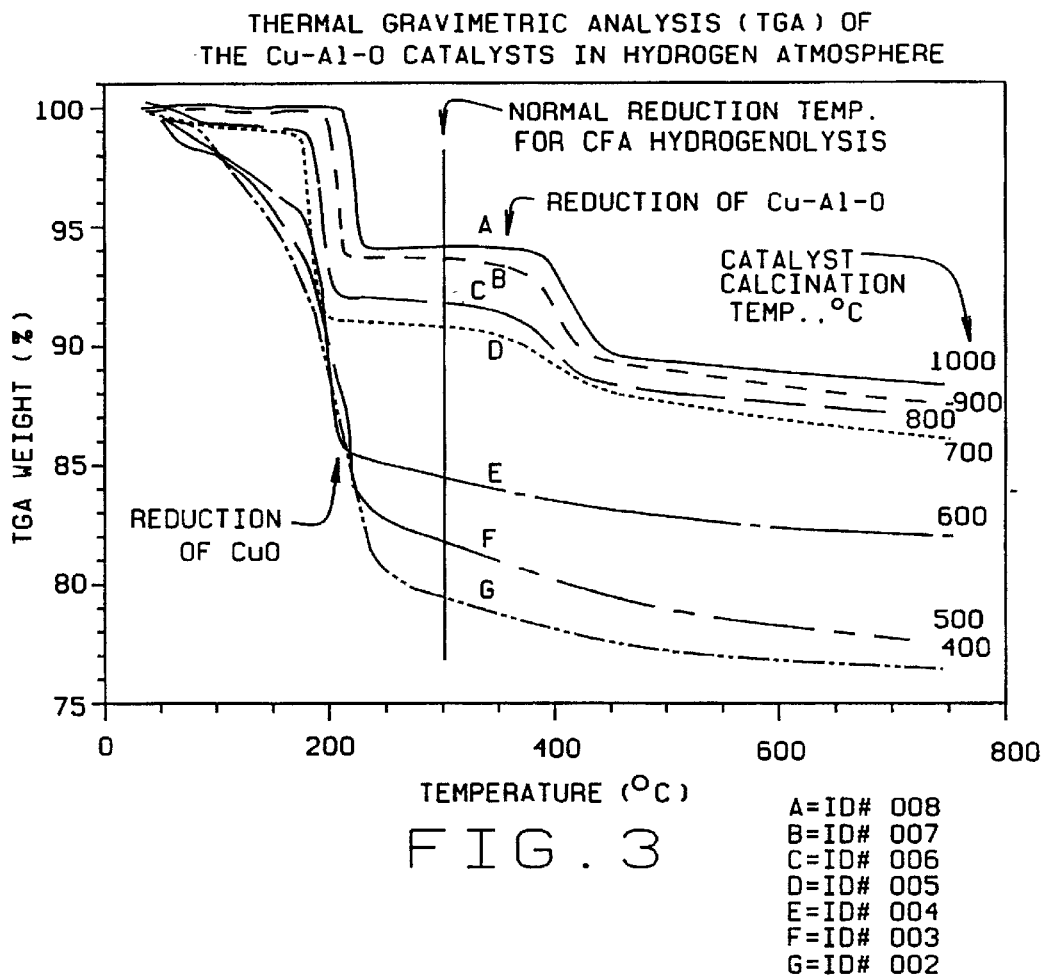
FIG. 3 illustrates the thermal gravimetric analysis (TGA) of the Cu—Al—O catalysts in hydrogen atmosphere.

A series of laboratory prepared Cu—Al—O catalysts of the present invention calcined at different temperatures were characterized by thermal gravimetric analysis (TGA). TGA experiments were run under both hydrogen and nitrogen atmospheres. As stated above, copper aluminate spinel crystal phase, as well as cupric oxide (CuO) phase, appear as calcination temperatures increase to >700° C. TGA results, as shown in FIG. 3, illustrate that there are two stages of weight loss if the catalyst was calcined at higher than 700° C. The first weight loss occurred at approximately 150° to 200° C., depending upon the calcination temperature. By correlating the results with the XRD measurement results, as discussed above, the weight lost in this temperature range corresponds to the reduction of cupric oxide. The second weight loss occurred at 350° C. to 400° C. and corresponds to the reduction of copper aluminate. The second weight loss only occurred with catalysts calcined at 700° C. or higher temperatures.

TABLE 1

Effect of Calcination Temperatures on Cu-Al-O Catalysts Properties

| Ex. No. | Catalyst ID | Calcination Temp. ° C. | Particle Size micron | | | Cu %, leachable | Al %, leachable | Surface Area, $m^2/g$ |
| --- | --- | --- | --- | --- | --- | --- | --- | --- |
| | | | dv, 10% | dv, 50% | dv, 90% | | | |
| Cu/Cr Control | 001 | | 1.8 | 15.7 | 62.6 | 4.3 | 0.7 (Cr) | 26 |
| 1 | 002 | 400 | 3.5 | 11.5 | 29.7 | 27 | 3.27 | 188 |
| 2 | 003 | 500 | 3.3 | 10.4 | 25.3 | 37.1 | 13.1 | 167 |
| 3 | 004 | 600 | 3.5 | 10.3 | 22.7 | 6.9 | 4.00 | 114 |
| 4 | 005 | 700 | 2.7 | 8.9 | 28.3 | 3.9 | 1.90 | 73 |
| 5 | 006 | 800 | 2.1 | 8.7 | 22 | 2.3 | 0.58 | 39 |
| 6 | 007 | 900 | 1.7 | 6.8 | 21.1 | 2.0 | 0.33 | 14 |
| 7 | 008 | 1000 | 1.3 | 5.5 | 26.8 | 0.77 | 0.10 | 7 |

As the calcination temperature increases the percentage of weight loss from the first weight loss (150° C. to 200° C.) decreases while the percentage of weight loss from the second weight loss (350° C. to 400° C.) increases. It will be noted that the percentage of weight loss at each of the two weight loss stages are approximately the same for catalyst calcined at 900° C.(Example 6) and 1000° C. (Example 7). That is, the copper content of the CuO and $CuAl_2O_4$ are about the same. The fingerprint characteristics of the TGA in $H_2$, as illustrated in FIG. 3, provide a convenient and reliable method for identifying and quantifying the formation of spinel copper aluminate.

EXAMPLE 11

Particle Size and Surface Area

Figure 4:
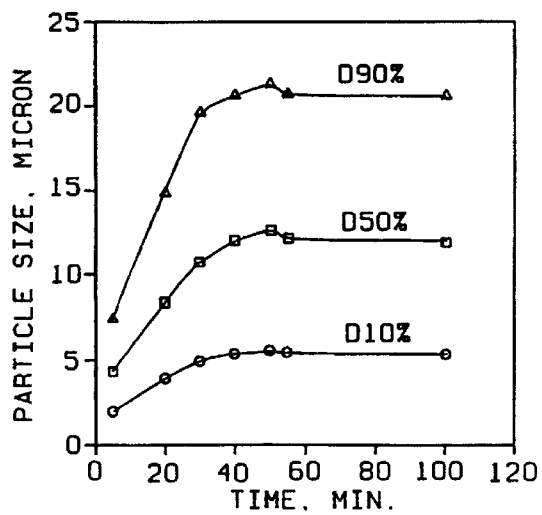
FIG. 4 is a graph illustrating particle size distribution of the Cu—Al—O catalyst of the present invention as a function of precipitation time.

FIG. 4 illustrates the precipitate particle size at different time periods in Example 1. It should be noted that the particle size becomes larger as the precipitation time goes on in the first hour of the precipitation procedure described in Example 1. The particle size remains constant after the first hour. Therefore, at a constant temperature, pH value and agitation speed, the precipitate particle size can be controlled by adjusting the slurry concentration.

As illustrated in Table 1 above, the particle size decreased marginally as the calcination temperature increased. The particle size, however, is within the range of commercial Cu/Cr catalysts.

It should be noted, however, that the surface area shrank more than 25 times from 188 $m^2/g$ to 7 $m^2/g$ as the calcination temperature increased from 400° C. (Example 1, Table 1) to 900° C. (Example 6, Table 1) while the catalytic activity remained almost the same, as will be explained in greater detail below. The decrease in surface area without a loss in catalyst activity suggests that most of the surface area is in micro-pores and is inaccessible by large reactant molecules such as fatty acids or ester.

EXAMPLE 12

Thirty (30) Gallon Scale-Up

The Cu—Al—O catalyst preparation, as provided in Example 1, was scaled-up to a 30 gallon tank. The particle size distribution and surface area are similar to the small scale preparation. The particle size distribution versus precipitation time of catalyst ID #009 is illustrated below in Table 2.

TABLE 2

Particle Size Distribution of 30 Gallon Precipitation
(Catalyst ID #009)

| Time (min.) | D-10% | D-50% | D-90% |
| --- | --- | --- | --- |
| 10 | 3.0 | 8.3 | 19.9 |
| 20 | 3.3 | 9.1 | 22.8 |
| 30 | 3.9 | 9.9 | 23.0 |
| 40 | 3.9 | 9.5 | 21.2 |
| 50 | 4.2 | 10.4 | 23.3 |
| 60 | 4.1 | 10.4 | 24.9 |
| 70 | 4.2 | 10.2 | 24.3 |
| 83 | 4.1 | 10.2 | 25.3 |

Other chemical and physical properties of the 30 gallon scale-up are compared to the laboratory preparation. To compare the results, the 30 gallon scale-up prepared powder was calcined at 800° C. (catalyst ID #10) for surface area and leachable Cu and Al analyses. The comparisons are illustrated below in Table 3.

TABLE 3

Comparison of Some Chemical/Physical Properties of Cu-Al-O
Catalysts From 30 Gallon, Pilot Plant Tank with Lab Preparation

|  | Example 12 | Example 5 | Example 13 |
| --- | --- | --- | --- |
| Scale | 30 gallon | Lab | Pilot Plant |
| Leachable Cu, % | 1.84 | 2.17 | 1.67 |
| Leachable, Al, % | 0.47 | 0.6 | 0.54 |
| Leachable Na, ppm | 377 | 200 | 50 |
| Surface Area, $m^2/g$ | 31 | 35 | 27 |
| LOI, (950° C.) | 0.95 | 1.95 | 1.0 |
| D-10%, $\mu m$ | 5.5 | 4.1 | 4.3 |
| D-50%, $\mu m$ | 13.9 | 10.3 | 10.7 |
| D-90%, $\mu m$ | 29.8 | 25.1 | 21.8 |

As shown in Table 3, the leachable copper is less than 2% and the leachable aluminum is less than 1%.

EXAMPLE 13

Pilot Plant Scale-Up Trial

The catalyst of the present invention was made on a larger scale and the chemical and physical properties were analyzed. The scale up factor is 190 times of is Example 1. The analytical results of powder made from the pilot plant scale-up also is listed in Table 3, above. As shown in Table 3, the catalyst calcined at 800° C. had particle size distributions of D-10% 4.3 $\mu m$, D-50% 10.7 $\mu m$, and D-90% 21.8 $\mu m$. These distributions are approximately the same values as found in the laboratory preparation. Furthermore, the surface area, leachable cations and loss on ignition (LOI) are similar to the lab preparations. The calcined powder particle size and distribution of the Example 13 are similar to Example 5.

Precipitation Variables

The effects of mixing speed and feed pump rate on particle size were studied.

EXAMPLE 14

Mixing Speed

Two mixing speeds, 410 rpm and 710 rpm were tested. Preliminary lab results, shown below in Table 4, indicate that mixing speed does not dramatically affect precipitate particle size distribution. However, high mixing speed, e.g. 710 rpm, gives smaller particle size.

TABLE 4

Effects of Mixing Speed (RPM) on Slurry Particle Size

| RPM | D-10% | D-50% | D-90% |
| --- | --- | --- | --- |
| 410 | 3.9 | 13.4 | 35.2 |
| 714 | 3.6 | 10.1 | 21.42 |

EXAMPLE 15

Feed Pump Rate:

The effects of the copper and aluminum solution feed pump rates on the particle size were studied. The precipitation details are the same as Example 1, the differences in this series of experiments are their feed pump rates. As shown in Table 5, rate at which the copper and aluminum solutions are fed into the precipitation does not appear to affect slurry particle size.

TABLE 5

Effects of Feed Pump Speed on Slurry Particle Size Distribution

| Feed Pump Rate, ml/min | D-10% | D-50% | D-90% |
|---|---|---|---|
| 15.2 | 3.8 | 11.1 | 25.6 |
| 26.3 | 3.6 | 10.1 | 21.4 |
| 55 | 3.5 | 9.3 | 20.4 |
| 73 | 3.8 | 10.5 | 28.7 |

As shown by the above data, the slurry particle size remains almost constant as the feed pump rates increased from 15 ml/min to 73 m/min.

EXAMPLE 16

Effects of Sodium Content on Catalyst Properties

Table 6, below, illustrates the chemical and physical properties of the Cu—Al—O catalyst of the present invention with different sodium content. The precipitation to details are the same as Example 1, except the washing. All of these catalyst were calcined at 800° C. for 2 hours.

TABLE 6

Physical/Chemical Properties of Cu-Al-O Catalysts with Different Sodium Content

| Catalyst I.D. # | 011 | 012 | 013 | 014 | 015 | 016 |
|---|---|---|---|---|---|---|
| CuO % | 51.7 | 55.8 | 58.3 | 58.0 | 59.6 | 58.5 |
| $Al_2O_3$ % | 32.8 | 35.4 | 37.3 | 37.9 | 37.5 | 37.37 |
| $Na_2O$ % | 5.26 | 2.70 | 1.29 | 0.36 | 0.09 | 0.02 |
| LOI % (950° C.), | 3.72 | 3.86 | 2.72 | 1.98 | 2.35 | 1.95 |
| Leachable Cu, % | 2.04 | 8.80 | 7.89 | 2.32 | 2.30 | 2.17 |
| Leachable Al, % | 4.05 | 2.41 | 1.42 | 0.72 | 0.76 | 0.60 |
| S. A. $m^2/g$ | 24 | 44 | 48 | 42.7 | 41.5 | 35 |

All the catalysts were prepared from the same batch. Catalyst ID #011 is a catalyst prepared without washing. Catalysts ID #'s 012 through 016 are catalysts prepared with one, two, three, four and five washes respectively. Each wash uses 3000 ml distilled water. Table 6 above showed that the preferred number of washings, i.e. four, reduces the $Na_2O$ content to <1% in the catalyst.

Generally speaking, the lower the sodium content, the lower the cation leachability will be. However, the leachable Cu in catalysts ID #011 is unexpectedly low, e.g. 2.04, as is the surface area, e.g. 24. There is not a clear relationship between the surface area and sodium content.

Figure 5:
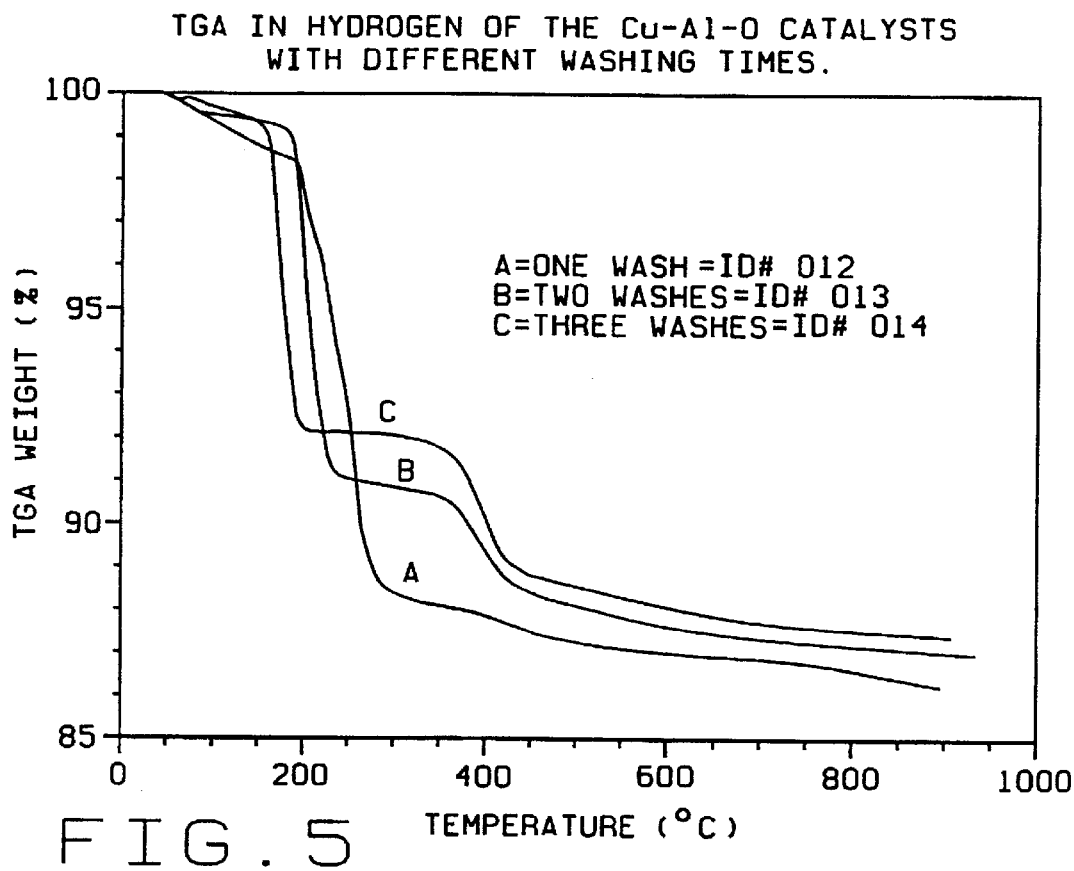
FIG. 5 illustrates the thermal gravimetric analysis (TGA) in hydrogen of the Cu—Al—O catalysts at different numbers of washings.

As stated above, Example 10, TGA in $H_2$ can be used as a quick method for identifying the spinel structure formation in the Cu—Al—O catalyst. The weight lost in the region of 150° to 200° C. is the reduction of CuO and the weight lost in the region of 350° to 400° C. corresponds to the reduction of spinel copper aluminate. A series of five Cu—Al—O catalysts, all calcined at 800° C., each having a different sodium content were characterized by TGA in hydrogen. For simplicity, the results from only three of the catalysts were shown in FIG. 5.

Curves A, B and C are the hydrogen reduction profiles of catalysts washed one, two and three times respectively to remove sodium. As illustrated, curves A, B and C have different profiles when heated in hydrogen. As shown in curve A there is almost no weight loss corresponding to reduction of spinel copper aluminate. Further, the reduction temperature for CuO was shifted to a higher temperature. Curve B indicates that the reduction of copper aluminate appears at approximately 350° to 400° C. and the reduction temperature for the CuO is lower than curve A. Curve C represents the catalyst washed three times. The weight loss of this catalyst corresponding to the reduction of copper aluminate was further increased and the CuO reduction temperature was decreased. This indicates that residual sodium in the catalyst not only retards copper aluminate formation, but also increases CuO reduction temperature.

EXAMPLE 17

Effects of Cupric Oxide (CuO) Content on Filtration Speed

One of the important characteristics of powder catalysts is their filterability. The Cu—Al—O catalyst of the present invention typically contains ~60% CuO. A series of catalysts with different CuO loadings were prepared. All of the catalysts were tested for filterability. The initial results indicated that the catalyst particle sizes have wider distribution as the CuO content increases. The wider distribution basically is caused by an increase in the number of smaller particles. Therefore, filtration speed decreases as the particles size distribution broadens.

Table 7 shows the filtration speed test of Cu—Al—O catalysts of the present invention along with commercially available Cu/Al or Cu/Cr catalysts, #017 and #001. The filtration speed tests were performed by the following procedures: 15 g of powder catalyst was dispersed in 100 ml deionized water by stirring 5 minutes. Filtration speed was tested under 18 inches vacuum with 5.5 cm diameter #42 Whatman filter paper. The time in Table 7 was recorded when solid first appeared in the funnel.

TABLE 7

Filtration Speed Test of Cu-Al-O Catalyst

| Catalyst # | Catalyst Component | CuO, % | Vacuum, inch | Time, |
|---|---|---|---|---|
| 018 | $CuO,Al_2O_3$ | 61% | 18 | 2'37" |
| 019 | $CuO,Al_2O_3$ | 70% | 18 | 4'39" |
| 020 | $CuO,Al_2O_3$ | 80% | 18 | 6'17" |
| 017* | $CuO,Al_2O_3$ | ~82% | 18.5 | 35' |
| 001* | $CuO,Cr_2O_3$ | ~47% | 18 | 4'53" |

*commercially prepared catalysts

The results, as illustrated in Table 7, indicate that filtration speed of the Cu—Al—O catalyst of the present invention is comparable to Cu/Cr catalyst #001. More importantly, it should be noted that the Cu—Al—O catalyst #020 and the commercial Cu—Al—O #017 have similar composition but the filtration speed of the catalyst prepared by the method of the present invention can be filtered five (5) times faster than the commercially prepared catalyst (#017).

PREPARATION OF CATALYST TABLETS AND EXTRUDATES

EXAMPLE 18

Cu—Al—O Catalyst Tablets

Catalyst powders for tablet formation were prepared according to Example 1 with different calcination temperatures ranging from 300° to 800° C. The calcination temperatures and Scott densities of each sample of calcined powders are listed below in Table 8.

TABLE 8

Properties of the Powders for Slugging

| Powder I.D. # | Calcination Temp. °C. | Scott Density, g/ml |
|---|---|---|
| 021 | 300 | 0.26 |
| 022 | 500 | 0.26 |
| 023 | 600 | 0.34 |
| 024 | 700 | 0.32 |
| 025 | 800 | 0.32 |

Tablets were made from the powders after the powder was mixed with 5% graphite powder, slugged and granulated. Powder #025 had good flow characteristics. The tablets made from Powder #025 had a good overall appearance. However, the side crush strength was only approximately 3 to 4 pounds for 1/8" by 1/8" tablet.

The tablets may be formed in numerous standard sizes, such as 1/8" by 1/8", 3/16" by 3/16", 1/4" by 1/4", 3/16" by 1/4", or 1/4" by 1/16", as is known in the art.

Tablets also were made from Powder #022. Four 1/8 inch by 1/8 inch sample of tablets, T-1, T-2, T-3 and T-4 were made from powder #022 and were tested for their physical properties (Table 9). The results of these test are included in Table 9:

TABLE 9

The Physical Properties of 1/8" × 1/8" Tablets

| Tablet # | T-1 | T-2 | T-3 | T-4 |
|---|---|---|---|---|
| Side crush Strength lb | 26.9 | 14.4 | 12.3 | 15.4 |
| Packed Bulk Density, g/ml | 1.08 | 1.00 | 0.91 | 0.93 |
| Pore Volume, ml/g | 0.39 | 0.43 | 0.49 | 0.45 |
| Pill weight, g | 0.046 | 0.044 | 0.039 | 0.048 |
| Length, in | 0.130 | 0.132 | 0.131 | 0.151 |
| Diameter, in | 0.125 | 0.125 | 0.125 | 0.125 |
| Pill Density, g/ml | 1.77 | 1.69 | 1.50 | 1.85 |
| Pill Feed Scott Density, g/ml | 0.529 | 0.529 | 0.529 | 0.494 |
| Graphite Powder | 5% | 5% | 5% | 2% |

It should be noted that the side crush strength was relatively high, e.g. from 12.3 lb. to 26.9 lb. while the bulk density is relatively low, e.g. from 0.91 g/ml to 1.08 g/ml.

EXAMPLE 19

Effects of Tablet Density on Pore Size Distribution

The relationship between bulk density and crush strength was investigated. The goal was to obtain an acceptable crush strength with a lower bulk density. Furthermore, the effect of tablet density on pore size distribution was investigated.

Figure 6:
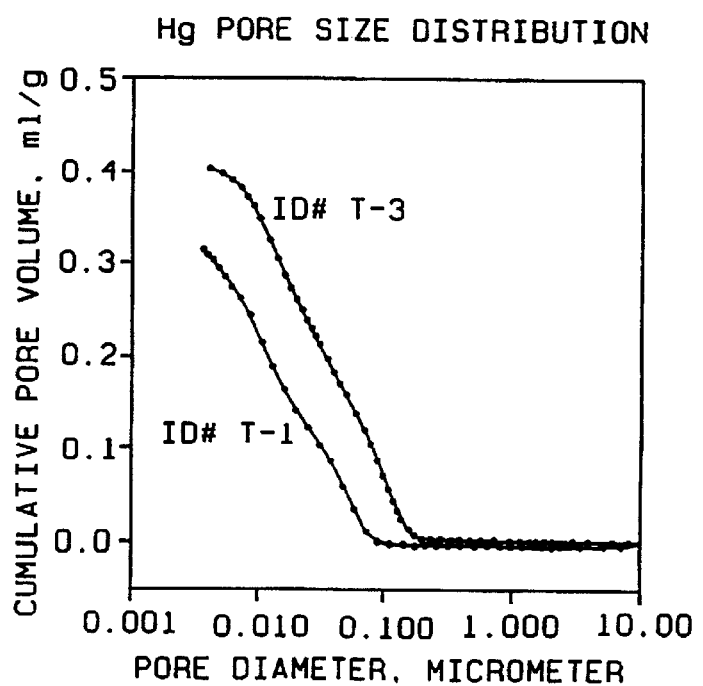
FIG. 6 is a graph illustrating pore size distribution of catalyst tablets having different densities.

The Hg pore size distribution of Tablet T-1 and Tablet T-3 are shown in FIG. 6. It is clear from FIG. 6 that the tablet density has a strong effect on the pore size distribution in the range of 900 Å to 1100 Å. The difference in total pore volume between Tablet T-1 and Tablet T-3 is due to the difference in pore volume at this region (900 Å to 1100 Å). There is no obvious effects of tablet density on the pore size smaller than 900 Å.

EXAMPLE 20

Effects of Different Tablet Size on the Physical Properties

Two different size tablets were made from powder catalyst ID #023. As shown in Table 8, catalysts ID #023 was calcined at 600° C. and had a Scott density of 0.34 g/ml. The tablets were given catalyst identification numbers of T-5 and T-6. The physical properties of the tablets are illustrated in Table 10.

TABLE 10

Some of Physical Properties of the Different Tablet Size

| Tablet ID # | T-5 | T-6 |
|---|---|---|
| Tablet Size, inch × inch | 3/16 × 3/16 | 3/16 × 1/8 |
| Length, in. | 0.194 | 0.134 |
| Diameter, in. | 0.189 | 0.190 |
| Weight, g. | 0.144 | 0.109 |
| Pill Density, g/ml | 1.60 | 1.73 |
| Side Crush Strength, lb | 23.7 | 31.7 |
| Bulk Density, g/ml | 0.989 | 1.13 |
| Pore Volume, ml/g | 0.41 | 0.34 |

As can be appreciated from Table 10, the tablets have a good side crush strength (>20 lb.) while the bulk density (B.D.) remains relatively low, 0.989 g/ml and 1.13 g/ml. and the pore volume (>0.34 ml/g) remains relatively high.

EXAMPLE 21

Effect of Tablet Density on Tablet Physical Properties

The effect of tablet density on other physical properties was studied in 1/8 inch by 1/8 inch tablets. All of the tablet feeds were made from the same batch of catalyst powder. The powder was calcined at 600° C. for 4 hours. Two groups of tablets were made, each group having a different graphite content. The first group, containing catalyst tablet identified at ID#'s T-7, T-8 and T-9 contained 2% graphite. The second group, containing catalyst tablets ID#'s T-10, T-11 and T-12 contained 1% graphite. Table 11 illustrates some of the physical properties of the tablets.

TABLE 11

Some of the Physical Properties of the Tablets

| Catalyst ID # | Graphite Content, % | Tablet Density, g/ml | Packed bulk Density, g/ml | Crush Strength lb | Pore Vol. Ml/g (Hg) | Size, LXD, inch × inch |
|---|---|---|---|---|---|---|
| T-7 | 2 | 1.72 | 0.97 | 13.4 | 0.374 | 0.129 × 0.125 |
| T-8 | 2 | 1.83 | 1.09 | 21.3 | 0.337 | 0.131 × 0.125 |
| T-9 | 2 | 1.98 | 1.23 | 36.6 | 0.239 | 0.130 × 0.126 |
| T-10 | 1 | 1.60 | 0.97 | 11.3 | 0.390 | 0.129 × 0.125 |
| T-11 | 1 | 1.75 | 1.08 | 20.8 | 0.328 | 0.130 × 0.126 |
| T-12 | 1 | 2.01 | 1.23 | 43.9 | 0.258 | 0.130 × 0.126 |

As shown, the crush strength increases dramatically with tablet density. Since there is a correlation between crush strength and tablet density, and if all the other factors are equal, the targeted crush strength can be reached by selecting the appropriate tablet density. It can be seen from Table 12 that a target pore volume can be obtained by controlling tablet density.

Furthermore, four different densities of 3/16 inch by 3/16 inch tablets were made. These four tablets were designated by ID#'s T-13, T-14, T-15 and T-16. The physical properties of the four tablets are shown in Table 12.

TABLE 12

Physical properties of 3/16" × 3/16" Cu-Al-O Tablets

| Tablet ID # | Graphite % | Length in. | Diameter, in. | Pill Density g/ml | Bulk Density g/ml | Crush Strength lb | Pore Volume (Hg) ml/g |
|---|---|---|---|---|---|---|---|
| T-13 | 2 | 0.174 | 0.189 | 1.43 | 0.84 | 19.9 | 0.43 |
| T-14 | 2 | 0.172 | 0.190 | 1.60 | 0.91 | 30.0 | 0.37 |
| T-15 | 5 | 0.172 | 0.190 | 1.33 | 0.81 | 16.2 | 0.48 |
| T-16 | 5 | 0.172 | 0.190 | 1.46 | 0.88 | 26.9 | 0.39 |

Figure 7:
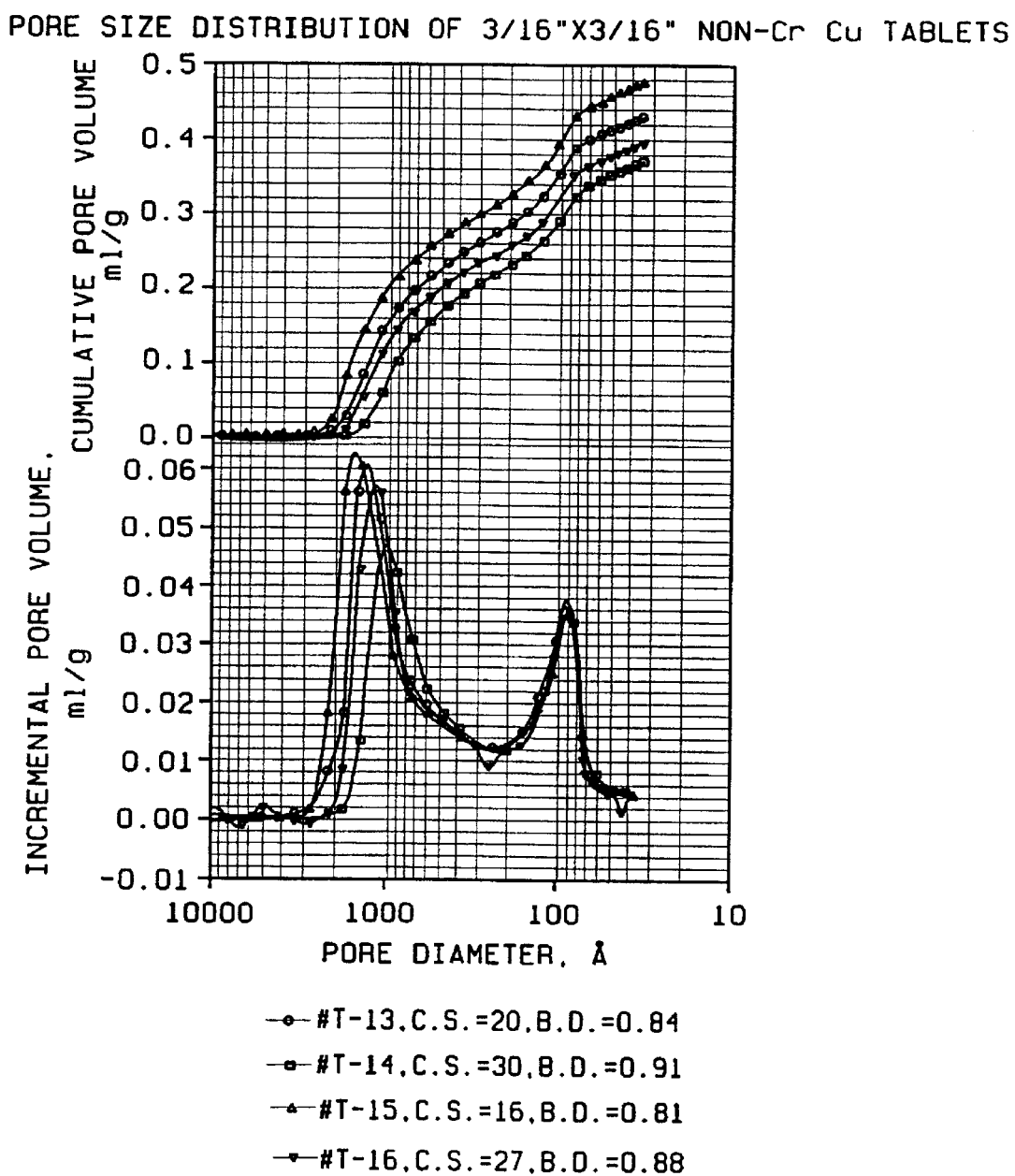
FIG. 7 is a graph illustrating cumulative and incremental pore volume of 3/16 inch by 3/16 inch catalyst tablets.

As best illustrated in FIG. 7, catalyst density only affects macro-pore volume, i.e. pore diameter from 0.07 micron to 0.3 micron (700 Å to 3000 Å), with almost no effect on pore sizes small that 0.02 micron (200 Å).

EXAMPLE 22

Cu—Al—O Catalyst Extrudate

A series of 1/16 inch Cu—Al—O extrudates were prepared from different powder feeds. LOD (Loss on Drying) of these powder feeds having from 35% to 42.5%. The extrudates were dried at 120° C. overnight followed by calcination at 500° C. for 3 hours. The basic physical properties of the samples are listed in Table 13.

TABLE 13

Physical and Chemical Properties of Cu-Al-O 1/16" Extrudate

| | |
|---|---|
| Crush Strength, lb | 5.4 |
| CuO % | 54.75 |
| $Al_2O_3$ % | 42.10 |
| Na % | 0.07 |
| Attrition, (30 mesh) | 2.1% |
| Hg Pore Volume, ml/g | 0.48 |
| BET, $m^2/g$ | 138 |
| LOI, % | 3.38 |
| Bulk Density g/ml | 0.68 |
| Bulk Crush Strength, @ 150 psig, 30 min. | 0.35% |

Normally monovalent acids, such as HCl, $HNO_3$, acetic acid or formic acid are used for controlling rheology. Organic acids are preferred because of no chloride corrosion and no $NO_x$ emission when the acid decomposes.

Figure 8:
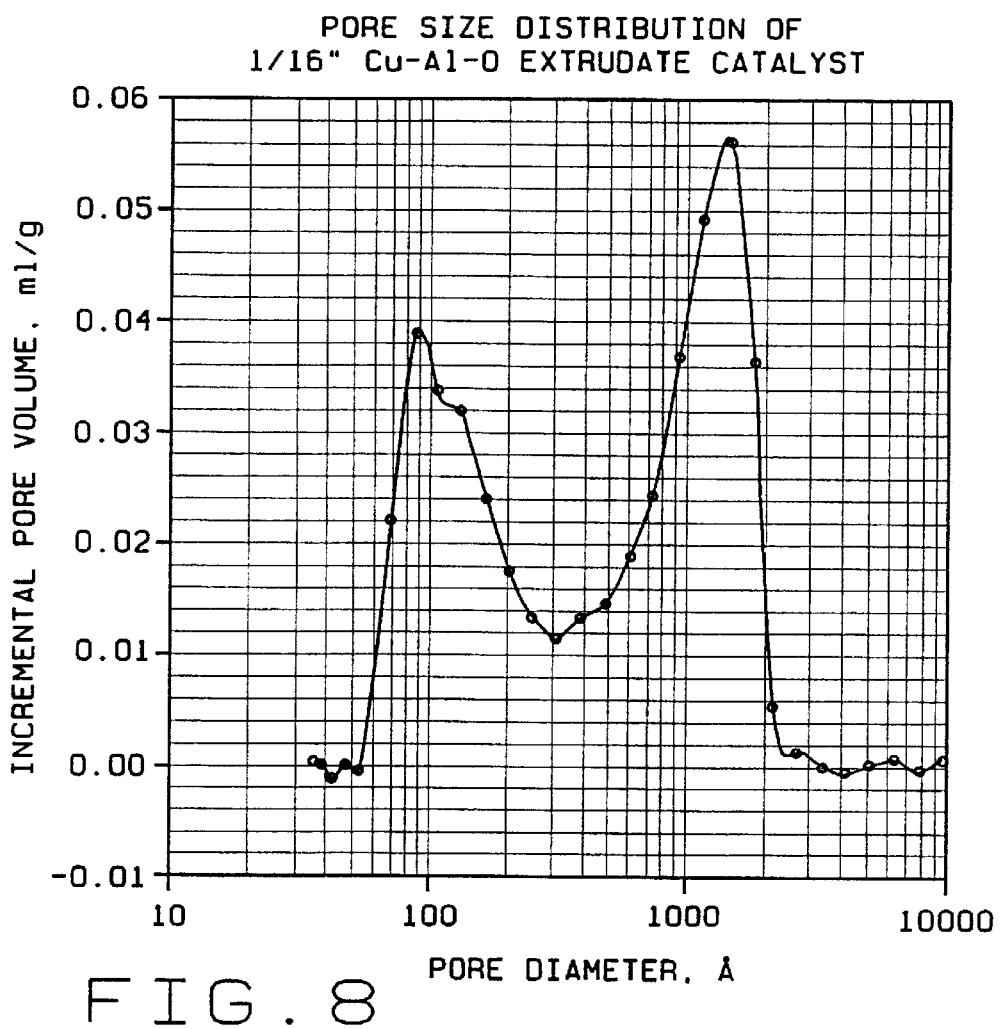
FIG. 8 is a graph illustrating incremental pore size distribution of a 1/16 inch catalyst extrudate.

In this invention, the extrudate samples were prepared without using any binder or peptizer. The samples were prepared directly from dried powder with LOD=40%. After calcination at 500° C., the average crush strength is above 5 lb. The final extrudate pore volume and pore size can be controlled by mulling time. As shown in FIG. 8, the prepared sample has bimodal pore size distribution centered at ~100 Å and 1500 Å and has a pore volume and pore size distribution similar to the 1/8 inch tablet form.

APPLICATIONS USING THE Cu—Al—O CATALYST OF THE PRESENT INVENTION

EXAMPLE 23

Oxoalcohol Finishing

The oxoalcohol finishing activities of tablets ID #'s T-1 and T-3 were tested side by side with commercial Cu/Cr catalyst ID #T-17. The physical properties of T-1 and T-3 are listed in Table 9, above. Tablet T-3 has the same chemical composition as T-1. However, there is a difference in their bulk densities, pore volume and pore size distribution. The packed bulk density of commercial Cu/Cr catalyst T-17 is approximately 1.52 times that of the tested Cu—Al—O catalysts of the present invention and T-17 has approximately 26% more CuO. The primary test results are shown in Table 14.

TABLE 14

Oxoalcohol Activity Test of 1/8" × 1/8" Cu-Al-O Tablets vs. Commercial Catalyst 1/8" × 1/8" Cu/Cr Tablet

| Catalyst: T-1, 40 ml, B.D. = 1.05 g/ml, 42 g catalyst contained 20.43 g CuO. | |
|---|---|
| Carbonyl Conv, % | 80 |
| Acid Conv., % | 34 |
| Ester Conv., % | 51 |
| Catalyst: T-3, 40 ml, B.D. = 0.91 g/ml, 35.85 g catalyst, contained 16.95 g CuO | |
| Carbonyl Conv. % | 84 |
| Acid, Conv., % | 50 |
| Ester Conv., % | 58 |
| Catalyst: T-17 1/8" tablet, 40 ml. B.D. = 1.594 g/ml, 63.76 g catalyst, contained 25.74 g CuO. | |
| Carbonyl Conv, % | 85 |
| Acid Conv., % | 37 |
| Ester Conv., % | 51 |

*Reaction conditions: $H_2$ flow rate = 180 scc/min. P = 1150 psig. LHSV = 2.2 $hr^{-1}$, water = 1.15%, T = 128° C. Time on stream = 180 hours.

*Reaction conditions: $H_2$ flow rate=180 scc/min. P=1150 psig. LHSV=2.2 $hr^{-1}$, water=1.15%, T=128° C. Time on stream=180 hours.

Table 14 shows that after 180 hours test, T-3 has similar activity with commercial Cu/Cr catalyst T-17, but T-1 has 5% lower conversion on carbonyl conversion. However, for more porous table catalyst, T-3 of this invention, Table 14 clearly shows that T-3 has a higher activity than T-17 and T-1. Ester and acid conversion are significantly greater than T-17. Further, the results indicated that under given reaction conditions, oxoalcohol finishing reaction on catalyst T-1 is diffusion limited.

To better compare the novel Cu—Al—O catalyst with commercial catalyst in oxoalcohol finishing, catalyst powder ID #022 was made into tablets (ID #T-18) of a similar size (3/16 inch by 3/16 inch) to a commercial Cu/Cr catalyst, T-19. These catalysts were pre-reduced and stabilized in isodecyl alcohol (TRL). The catalyst activity was tested compared to commercial Cu/Cr catalyst designated as T-19. The results are shown in Table 15.

TABLE 15

Oxoalcohol Activity Test* of 3/16" × 3/16"
Cu-Al-O TRL** vs. Cu/Cr TRL T-19

Catalyst: T-18, 3/16" TRL, 70.72 g/60 ml

| HOS, hr | 19 | 43 | 69.3 | 91 |
|---|---|---|---|---|
| Carbonyl Conv, % | 84.4 | 85.8 | 84.7 | 83.5 |
| Acid Conv., % | 41.8 | 41.0 | 54.8 | 54.1 |
| Ester Conv., % | 62.6 | 61.7 | 61.4 | 60.3 |

Catalyst: T-19 ~3/16" TRL, 106.11 g/60 ml,

| HOS, hr | 19 | 43 | 69.3 | 91 |
|---|---|---|---|---|
| Carbonyl Conv. % | 86.9 | 88.9 | 87.0 | 86.2 |
| Acid, Conv., % | 33.3 | 38.9 | 49.3 | 49.4 |
| Ester Conv., % | 60.7 | 63.9 | 63.6 | 62.0 |

*Reaction conditions: $H_2$ follow rate = 180 scc/min. LHSV = 1.5 $hr^{-1}$, 1.15% $H_2O$, T = 152° C., P = 1200 psig.
** TRL -- catalyst reduced and stabilized in isodecyl alcohol.

The catalyst activities were tested for four days. The results shown in Table 15 indicate that the activities for acid and ester conversion are not significantly different between the two catalysts. The tests show that the catalyst activity for the novel Cu—Al—O catalyst in oxoalcohol finishing is approximately equivalent to that of commercial chromium containing catalyst. However, the Cu—Al—O catalyst is free of environmentally toxic chromium. The Cu—Al—O catalyst has a much lower bulk density than the Cr/Cu catalyst and, therefore, weighs ½ to ⅔ of the commercial available Cr/Cu catalyst.

EXAMPLES 24–28

Hydrogenolysis of Coconut Fatty Acid (CFA)

The following Examples, 24–30, describe the application of Cu—Al—O catalysts of present invention to the hydrogenolysis of coconut fatty acid.

EXAMPLE 24

Effects of Calcination Temperature

Table 16 illustrates the catalytic activity of various Cu—Al—O catalysts of the present invention calcined at different temperatures. Catalyst ID #001 is the standard commercially available Cu/Cr catalyst.

The catalyst samples prepared from Example 1 to Example 7 are tested for the activity a selectivity of hydrogenolysis of coconut fatty acid to fatty alcohol.

TABLE 16

Effects of Calcination Temperatures on Cu-Al-O Catalysts Activity

| Example Number | Catalyst ID# | Calcination Temp* ° C. | Relative Activity** | Selectivity*** % |
|---|---|---|---|---|
| Cu/Cr Standard | 001 | 440 | 100 | 0.11–0.18 |
| 1 | 002 | 400 | 155 | 0.13 |
| 2 | 003 | 500 | 198 | |
| 3 | 004 | 600 | 152 | |
| 4 | 005 | 700 | 151 | 0.17 |
| 5 | 006 | 800 | 177 | 0.11 |
| 6 | 007 | 900 | 127 | 0.12 |
| 7 | 008 | 1000 | 62 | 0.25 |

*All catalysts were calcined in air.
**The relative activity is calculated by the ratio of rate constant of the catalyst with that of the standard Cu/Cr catalyst. The rate constants are measured in the reaction time from 5 minutes to 120 minutes with the assumption of 90% conversion under the equilibrium conditions.

TABLE 16-continued

Effects of Calcination Temperatures on Cu-Al-O Catalysts Activity

| Example Number | Catalyst ID# | Calcination Temp* ° C. | Relative Activity** | Selectivity*** % |
|---|---|---|---|---|

***Selectivity is defined as weight percent of dodecane at 1.5% ester remaining in the reactor.

As shown in Table 16, catalytic activity in hydrogenolysis of coconut fatty acids improved when the catalysts were calcined at higher temperatures. If the calcination temperature exceeds 800° C., the catalyst begins to lose activity. This apparently is due to the decomposition of cupric oxide and the spinel structure of Cu—Al—O in the catalyst. It will be appreciated that CuO is unstable at temperatures greater than 800° C. and it decomposes to $Cu_2O$ and $O_2$. A similar phenomenon was observed for $CuAl_2O_4$. In Ar atmosphere and at 870° C., the following reaction takes place:

$$4CuAl_2O_4 \rightarrow 4CuAlO_2 + 2Al_2O_3 + O_2$$

It is of interest to note that catalyst ID #003, which was calcined at 500° C., had a relative activity of 198% for hydrogenolysis of coconut fatty acid as compared to the standard, catalyst ID #001. As seen, there are two calcination temperature ranges corresponding to greater catalytic activity. The high catalytic activity of the catalyst calcined at 500° C., Example #2 may be explained. Example #2 (catalyst is ID #003), as shown in Table 1, had a higher percentage of leachable copper. The unusually high activity of that catalyst may be due to soluble copper in the reaction slurry. It is further noted from Table 16 that the catalyst activity was maximized where the catalyst was calcined at approximately 800° C. and decreased as the temperature increased beyond 800° C.

One of the concerns of hydrogenolysis of coconut fatty acid is the selectivity.

Table 16 shows that when Cu—Al—O catalyst of this invention is calcined at from 400° C. to 800° C., the selectivity for this reaction is equal or better than the standard commercial Cu/Cr catalyst.

EXAMPLE 25

Effects of Catalyst Promoters

Cerium oxide ($Ce_2O_3$) was tested as a promoter for the Cu—Al—O catalyst. Table 17 shows the catalytic activity of a series of catalysts with different doping amounts of $Ce_2O_3$ It should be noted that the selectivity of the Cu—Al—O catalyst for hydrogenolysis of coconut fatty acid is expressed as dodecane made at 1.5% ester remaining.

TABLE 17

Effects of $Ce_2O_3$ on the Catalytic Activity and Selectivity of Cu-Al-O

| Catalyst ID #* | $Ce_2O_3$ % | Calcination Temp ° C.** | S. A. $m^2/g$ | Relative Activity *** | Selectivity % *** |
|---|---|---|---|---|---|
| 001 | 0 | 440 | 26 | 100 | 0.12–0.23 |
| 005 | 0 | 700 | 73 | 151 | 0.17 |
| 026 | 10 | 700 | 50 | 159 | 0.11 |
| 027 | 5 | 700 | 51 | 165 | 0.11 |
| 028 | 2.5 | 700 | 55 | 164 | 0.09 |
| 029 | 2.5 | 700 | 55 | 172 | 0.11 |

*Catalysts number 026, 027 and 028 were prepared by impregnation method. Catalyst # 6 was prepared by co-precipitation method.

TABLE 17-continued

Effects of $Ce_2O_3$ on the Catalytic Activity and Selectivity of Cu-Al-O

| Catalyst ID #* | $Ce_2O_3$ % | Calcination Temp ° C.** | S. A. $m^2/g$ | Relative Activity *** | Selectivity % *** |
|---|---|---|---|---|---|

**All catalysts were calcined in air.
***Calculation method is the same as shown in Table 16.

Table 17 shows that $Ce_2O_3$ is an activity and selectivity promoter for fatty acid/ester hydrogenolysis when used with the Cu—Al—O catalyst in this invention. Further, it appears from the data that a 2.5% $Ce_2O_3$ doped catalyst gives a better activity and selectivity than 10% $Ce_2O_3$. MnO, BaO and Ni promoted Cu—Al—O catalysts in this invention have similar effects on the catalyst activity and selectivity.

EXAMPLE 26

Effect of Cupric Oxide Content of the Cu—Al—O Catalyst on Hydrogenolysis Activity A series of catalysts with different cupric oxide (CuO) content were tested for coconut fatty acid hydrogenolysis. The results are shown in Table 18.

Catalyst ID #031 gives the highest activity, 177% of the standard Cu/Cr catalyst #001. As the CuO content increases, the activity for CFA conversion drops. However, Table 18 shows that CuO content from 40% to 80% in the Cu—Al—O catalysts in this invention exhibits higher or equal (Catalyst ID #033) activity to the catalyst ID #001, the standard Cu/Cr catalyst.

TABLE 18

Effects of CuO content on CFA Activity

| Catalyst ID # | Catalyst Component | CuO, % LOI Free | CFA Activity, % of E-118 |
|---|---|---|---|
| 030 | CuO, $CuAl_2O_4$ | 41 | 159 |
| 031 | CuO, $CuAl_2O_4$ | 61 | 177 |
| 032 | CuO, $CuAl_2O_4$ | 70 | 126 |
| 033 | CuO, $CuAl_2O_4$ | 80 | 98 |
| 001 | CuO, $CuCr_2O_4$ | ~47 | 100 |

EXAMPLE 27

Effects of Sodium Content of the Cu—Al—O Catalyst on Hydrogenolysis

Table 19. below, shows the chemical and physical properties of Cu—Al—O catalysts of the present invention having different sodium contents. All of the catalysts were prepared from the same batch. However, the sodium content varied due to the amount of washing. As stated above with reference to Table 3, proper washing, i.e. four washes can reduce the sodium content to <1%.

Catalyst #001 was not washed. Catalysts #012, #013, #014, #015 and #16 were subjected to 1, 2, 3, 4 and 5 washings, respectively. Each washing use the same volume of de-ionized water.

TABLE 19

Physical/Chemical Properties and CFA Hydrogenolysis Activity of Cu-Al-O Catalysts with Different Sodium Content

| Catalyst I.D. # | 011 | 012 | 013 | 014 | 015 | 016 |
|---|---|---|---|---|---|---|
| CFA Activity of E-118, % | 11 | 22 | 69 | 138 | 158 | 175 |
| CuO % | 51.7 | 55.8 | 58.3 | 58.0 | 59.6 | 58.2 |
| $Al_2O_3$ % | 32.8 | 35.4 | 37.3 | 37.9 | 37.5 | 37.37 |
| $Na_2O$, % | 5.26 | 2.79 | 1.29 | 0.36 | 0.09 | 0.02 |
| LOI % (950° C.) | 3.72 | 3.86 | 2.72 | 1.98 | 2.35 | 1.95 |
| Leachable Cu, % | 2.04 | 8.80 | 7.89 | 2.32 | 2.30 | 2.17 |
| Leachable Al, % | 4.05 | 2.41 | 1.42 | 0.72 | 0.76 | 0.60 |
| S.A., $m^2/g$ | 24 | 44 | 48 | 43 | 42 | 35 |

Figure 9:
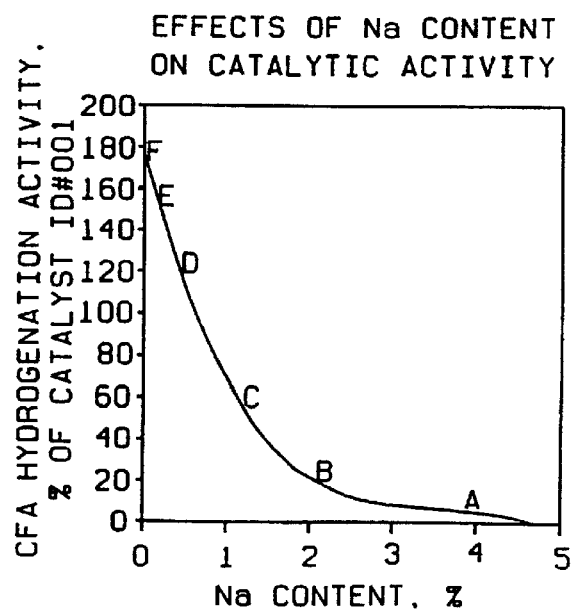
FIG. 9 is a graph illustrating the effect of sodium content of the Cu—Al—O catalyst of the present invention on catalyst activity; and letters A through F represent catalyst ID #011 through #016.

Generally, as indicated by the washed samples, the lower the sodium content, the lower the leachable cations (Cu and Al). The surface area and leachable copper in the unwashed sample is unexpectedly low. There is, however, a relationship between the low sodium content and activity on coconut fatty acid hydrogenolysis, as best illustrated in FIG. 9. The lower the sodium content, the better the catalytic activity. A sodium oxide content less than 0.5% produces optimal catalytic activity for this particular application.

EXAMPLE 28

Effect of Catalyst Reduction On Coconut Fatty Acid Hydrogenolysis

As shown above in Table 16, catalytic activity tests indicated that catalyst calcined at 1000° C. (catalyst ID #008) had reduced catalytic activity. The decreased activity originally was assumed to be due to difficulty in achieving catalyst reduction at that temperature. To determine if additional reduction would improve catalyst activity, catalyst ID #008 was further reduced an additional hour at 300° C. and 4400 psi hydrogen. The results are shown in Table 20.

TABLE 20

Effects of Reduction on Catalyst ID #008 Hydrogenolysis Activity

| Catalyst Reduction Condition | Activity, % of Standard Cu/Cr Catalyst ID #001 | Rate of Dodecane Formation, K* 1,000 | Dodecane % at 1.5% Ester remaining |
|---|---|---|---|
| 500 Psig $H_2$, heated from room temp. to 300° C., final pressure was 830 Psig | 62 | 2.9 | 0.25 |
| above + hold at 300° C. and 4400 Psig for one hour | 32 | 6.7 | 1.26 |

As can be seen, the extended reduction did not increase activity but dramatically decreased the activity and selectivity for this high temperature (1000° C.) calcined catalyst.

In a separate test, catalyst ID #034 calcined at 800° C., (similar composition to catalyst ID #16 and #31) was tested for hydrogenolysis activity at normal reduction and one hour extended reduction at 300° C. and 830 psig hydrogen. The results are shown in Table 21.

TABLE 21

Effects of Reduction on Catalyst ID #034 Hydrogenolysis Activity

| Catalyst Reduction Condition | Activity, % of Standard Catalyst #001 | Rate of Dodecane Formation, K*1,000 | Dodecane % at 1.5% Ester remaining |
|---|---|---|---|
| 500 Psi $H_2$, heated from room temp. to 300° C., final pressure was 830 Psig | 182 | 3.44 | 0.11 |
| above + hold at 300° C. and 4400 Psig for one hour | 186 | 4.25 | 0.13 |

As shown in Table 21, the extended reduction resulted in little change in the overall activity or the selectivity to hydrocarbon, as indicated by the dodecane % and rate of dodecane formation.

EXAMPLE 29

Hydrogenolysis of Methyl Laurate

Catalyst ID #T-3 of the present invention was tested for methyl laurate hydrogenolysis activity. The results are listed in Table 22.

TABLE 22

Hydrogenolysis of Methyl Laurate on Different Cu-based Catalysts

| Catalyst ID # | T-3 (Cu/Al) Cat. = 27.31 g/30 ml B.D. = 0.91 g/ml | T-20 (Cu/Cr) Cat. = 47.41 g/30 ml B.D. = 1.58 g/ml |
|---|---|---|
| | 185° C. | |
| LHSV, 1/hr* | 0.74 | 0.73 |
| WHSV, 1/hr** | 0.71 | 0.40 |
| Conv. % | 91.9 | 94.97 |
| | 200° C. | |
| LHSV, 1/hr | 0.74 | 0.74 |
| WHSV, 1/hr | 0.71 | 0.41 |
| Conv. % | 98.42 | 98.87 |

*Liquid hourly space velocity
**Weight hourly space velocity

It will be appreciated by those skilled in the art that the reaction temperature and LHSV in industrial applications are 200° C. and 0.5 to 1 hour$^{-1}$, respectively. Under industrial conditions the two catalysts will be active enough to reach equilibrium conditions. In fact, at 200° C., with LHSV=0.74 hr$^{-1}$, the reaction is close to equilibrium. Because of the large differences in bulk density between Cu—Al—O catalysts and Cu/Cr catalysts, the rate at the same weight and hourly space velocity (WHSV) of the novel Cu—Al—O catalysts are significantly higher than that of Cu/Cr catalysts.

Other Applications

The foregoing applications and characterizations demonstrate that the non-chrome containing Cu—Al—O catalysts of the present invention exhibits catalytic activity, selectivity and stability equal to or superior to the chromium containing copper catalysts presently employed in many commercial applications. In addition to this, Cu—Al—O catalyst of the present invention does not have the environmental problems associated with the conventional chromium containing copper catalysts.

Furthermore, it will be appreciated that the novel Cu—Al—O catalysts of the present invention may be employed in a large number of applications not specifically discussed herein. For example, the Cu—Al—O catalyst may be substituted for prior art catalysts disclosed above. By way of particular example, the Cu—Al—O catalyst of the present invention can be used in the hydrogenation applications disclosed in U.S. Pat. No. 5,243,095 to Roberts et al. These reactions may include, but are not limited to, a number of alkylation reactions, dehydrogenation reactions, hydrogenation reactions, reductive amination, hydrogenation of nitrites to unsaturated secondary amines, oxidation and reduction reactions. These include alkylation of phenol with alcohols; amination of alcohols; dehydrogenation of alcohols; hydration of nitrile; hydrogenation of aldehydes; hydrogenation of amides; hydrogenation of fatty acids via esterification and hydrogenolysis; selective hydrogenation of fats and oils; hydrogenation of nitrites; hydrogenation of nitroaromatic hydrocarbons; hydrogenation of ketones; hydrogenation of furfural; hydrogenation of esters; hydrogenation of carbon monoxide to methanol; oxidation/incineration of carbon monoxide; oxidation of vapor organic compounds (VOC); oxidation of $SO_2$; oxidation of alcohols; decomposition of nitric oxide; selective catalytic reduction of nitric oxide; and purification of a gas stream by the removal of oxygen.

Moreover, various changes and modifications may be made in the catalyst of the present invention, in the method of preparing the same, and in the reactions catalyzed by it, without departing from the scope of the appended claims. Therefore, the foregoing description and accompanying figures are intended to be illustrative only and should not be construed in a limiting sense.

What is claimed is:

1. A catalyst having a homogeneous bulk composition, the catalyst consisting essentially of oxides of copper and aluminum, less than 60% of the catalyst by weight comprising a spinel structure, the catalyst having less than about 10% leachable copper ions as determined by reacting 100 ml 10% acetic acid with 10 g of powder catalyst for one hour with continuous stirring.

2. A solid catalyst comprising a compressed homogeneous Cu—Al—O powder substantially free of chromium, the solid catalyst having a bimodal pore size distribution centering around 100 Å and around 500 Å to 2000 Å.

3. The catalyst of claim 1 having a calculated alumina content of about 20% to about 90% by weight and a calculated copper oxide content of about 80% to about 10% by weight.

4. The catalyst of claim 3 wherein the calculated alumina content is about 30% to about 60% by weight, and the calculated CuO content is about 70% to about 40% by weight.

5. The catalyst of claim 1 wherein at least a part of the alumina content and a part of the CuO content are $CuAl_2O_4$ in a spinel crystal structure, the spinel structure comprising less than 60% of the catalyst by weight.

6. The catalyst of claim 2 wherein the calculated CuO content is 61±20%.

7. The catalyst of claim 1 wherein the catalyst has less than about 5% leachable copper ions.

8. The catalyst of claim 1 wherein the catalyst is substantially free of chromium.

9. The catalyst of claim 1 further comprising a promoter, the promoter being present in an amount no greater than about 25% by weight of the catalyst.

10. The catalyst of claim 9 wherein the promoter is chosen from the group consisting of salts and oxides of Ce, Ba, Mn, Co, Zn, Ni, alkaline, and alkaline earth metals.

11. The catalyst of claim 10 wherein the promoter is chosen from the group consisting of salts and oxides of Ce, Mn, Ba and Ni.

12. The catalyst of claim 2 having a surface area of about 15 to about 250 m²/g.

13. The catalyst of claim 12 having a surface area of from about 15 to about 170 m²/g.

14. The catalyst of claim 1 having the formula $nCuO \cdot Al_2O_3$ wherein n is between 0.14 and 5.13.

15. The catalyst of claim 2 wherein the catalyst is a tablet formed with 0–8% lubricant.

16. The solid catalyst of claim 2 wherein the catalyst is a calcined extrudate of a Cu—Al—O powder.

17. The catalyst of claim 2 having a pore volume of approximately 0.15 ml/g to approximately 0.6 ml/g.

18. The solid catalyst of claim 2 having a bulk density of approximately 0.6 g/ml to approximately 1.5 g/ml.

19. The catalyst of claim 2 made from a powder having a homogeneous bulk composition, the catalyst consisting essentially of oxides of copper and aluminum, the catalyst having less than about 10% leachable copper ions as determined by reacting 100 ml 10% acetic acid with 10 g of powder catalyst for one hour with continuous stirring.

20. The catalyst of claim 2 further comprising a promoter, the promoter being present in an amount no greater than about 25% by weight of the catalyst.

21. A solid extrudate of a catalyst having a homogeneous bulk composition, the catalyst consisting essentially of oxides of copper and aluminum, the extrudate being substantially free of binder and peptizer.

22. The extrudate of claim 21 further comprising a promoter, the promoter being present in an amount no greater than about 25% by weight of the catalyst.

23. The extrudate of claim 22 wherein the promoter is chosen from the group consisting of salts and oxides of Ce, Ba, Mn, and Ni.

24. The extrudate of claim 21 having a surface area of about 15 to about 250 m²/g.

25. The catalyst of claim 1 wherein the calculated CuO content is 61±20%.

26. The catalyst of claim 1 having a surface area of about 15 to about 250 m²/g.

27. The catalyst of claim 26 having a surface area of from about 15 to about 170 m²/g.

28. The catalyst of claim 2 having a calculated alumina content of about 20% to about 90% by weight and a calculated copper oxide content of about 80% to about 10% by weight.

29. The catalyst of claim 28 wherein the calculated alumina content is about 30% to about 60% by weight, and the calculated CuO content is about 70% to about 40% by weight.

30. The catalyst of claim 2 wherein the catalyst is substantially free of chromium.

31. The catalyst of claim 20 wherein the promoter is chosen from the group consisting of salts and oxides of Ce, Ba, Mn, Co, Zn, Ni, alkaline, and alkaline earth metals.

32. The catalyst of claim 31 wherein the promoter is chosen from the group consisting of salts and oxides of Ce, Mn, Ba and Ni.

33. The catalyst of claim 2 having the formula $nCuO \cdot Al_2O_3$ wherein n is between 0.14 and 5.13.

34. The extrudate of claim 21 having the formula $nCuO \cdot Al_2O_3$ wherein n is between 0.14 and 5.13.

35. The extrudate of claim 21 having a pore volume of approximately 0.15 ml/g to approximately 0.6 ml/g.

36. The extrudate of claim 21 having a bulk density of approximately 0.6 g/ml to approximately 1.5 g/ml.

37. The extrudate of claim 21 made from a powder having a homogeneous bulk composition, the catalyst consisting essentially of oxides of copper and aluminum, the catalyst having less than about 10% leachable copper ions as determined by reacting 100 ml 10% acetic acid with 10 g of powder catalyst for one hour with continuous stirring.

38. The extrudate of claim 21 wherein the catalyst has a bimodal pore size distribution centering around 100 Å and around 500 Å to 2000 Å.

* * * * *